United States Patent [19]

Luce et al.

[11] Patent Number: 5,099,070

[45] Date of Patent: Mar. 24, 1992

[54] METHOD OF PRODUCING NEOPENTYLDIAMINE

[75] Inventors: Garrett C. Luce, Longview, Tex.; Anthony W. McCollum, Kingsport, Tenn.

[73] Assignee: Eastman Kodak Company, Rochester, N.Y.

[21] Appl. No.: 623,461

[22] Filed: Dec. 7, 1990

[51] Int. Cl.$^5$ ............................................. C07C 209/00
[52] U.S. Cl. .................................. 564/480; 564/473; 564/482; 564/503
[58] Field of Search ................ 564/480, 482, 473, 503

[56] References Cited

U.S. PATENT DOCUMENTS 2,618,658 11/1952 Caldwell .
4,078,003 3/1978 Feichtinger et al. .
4,495,369 1/1985 Werner et al. ...................... 564/480

Primary Examiner—Marianne Cintins
Assistant Examiner—Jessica H. Nguyen
Attorney, Agent, or Firm—Mark A. Montgomery; William P. Heath, Jr.

[57] ABSTRACT

A process for producing neopentyldiamine is provided. This process entails contacting a feedstream containing neopentanolamine with ammonia and hydrogen in the presence of a support nickel catalyst under amination conditions.

11 Claims, No Drawings

METHOD OF PRODUCING NEOPENTYLDIAMINE

FIELD OF THE INVENTION

The present invention relates to a process of preparing neopentyldiamine. The process of the present invention produces neopentyldiamine at high yield and conversion.

BACKGROUND OF THE INVENTION

Neopentyldiamine or neopentane diamine (1,3-diamino-2,2-dimethylepropane) is a valuable intermediate in the manufacture of polyurethanes, the polyamidimide resins and other condensation polymers.

The production of neopentyldiamine is generally known and has been prepared by reacting acetone with nitromethane to form 2,2-dimethyl-1,3-dinitropropane followed by hydrogenation of the dinitro compound. Improvements upon this process are disclosed in U.S. Pat. No. 4,078,003. This reference describes the synthesis of neopentyldiamine from neopentylglycol under particular reaction conditions such as reaction with ammonia in the presence of hydrogen and a nickel containing catalyst. Under the best conditions this process has a yield of 78% of theoretical. Improved conversion can be obtained by recycling unreacted materials.

It would be very desirable to be able to increase the conversion and yield of neopentyldiamine without significantly complicating the process.

SUMMARY OF THE INVENTION

The method of producing neopentyldiamine according to the present invention comprises contacting a C5 feedstream containing a high concentration of neopentanolamine with ammonia and hydrogen in the presence of a supported nickel catalyst under amination conditions.

DETAILED DESCRIPTION OF THE INVENTION

The present invention produces neopentyldiamine by a novel process using neopentanolamine as feedstock. The process of the present invention significantly increases conversion and yield of neopentyldiamine. This process also provides a lower yield of low boiling byproducts thus providing easier cleanup and isolation of the purified product.

The feedstock used in the present invention is a C5 feedstock containing a high amount of neopentanolamine or essentially pure neopentanolamine. It is important that the feedstock of the present invention be substantially free of neopentylglycol. Lower yields in the prior art process are believed to be due to the much easier hydrogenolysis of neopentylglycol as compared to neopentanolamine used according to the present invention. The feedstock preferably contains between about 90 and 100 weight percent neopentanolamine. Neopentanolamine is available and can be prepared for example by reductive amination such as disclosed in U.S. Pat. No. 2,618,658. Catalyst used in the process of the present invention must be a supported nickel catalyst since the desired reaction does not occur to a significant extent with other catalyst. The preferred catalyst used in the process of the present invention is a nickel catalyst on a predominantly alumina-containing support. The loading level of nickel on this support preferably falls within the range of about 10 to 75 weight percent with about 30 to 70 weight percent being more preferred and about 55 weight percent being most preferred.

The molar ratio of ammonia to neopentanolamine in the reaction mixture preferably falls within the range of about 1 up to 50 mols of ammonia per mol of neopentanolamine with about 5 to 25 mols of ammonia per mol of neopentanolamine being more preferred and about 18 to 21 mols of ammonia per mol of neopentanolamine being most preferred.

The weight ratio of neopentanolamine to catalyst generally falls within the range of about 1:1 up to 1,000:1 with about 5:1 up to 100:1 being more preferred.

The mol ratio of ammonia to hydrogen in the amination process of the present invention is at least 1:1 with the range of about 5:1 up to 20:1 being more preferred.

The amination conditions of the present invention generally require the reaction in the process of the present invention to be conducted at a temperature within the range of about 150° up to 250° C. However, below about 180° C. conversion is fairly low and above 220° C. hydrogenolysis to low boiling byproducts begins to predominate the reaction. Therefore, the react temperature preferably falls within the range of about 180° C. to 220° C. with about 200° C. being most preferred.

The pressure in the reactor is preferably within the range of about 1,500 to 4,500 psig. The reaction pressure more preferably falls within the range of about 2,800 to 3,400 psig with about 3,000 psig being most preferred.

The amination reaction conditions are preferably maintained for a time in the range of about 0.5 up to 5 hours. A reaction time of up to about 3 hours gives good product and selectivity with lower conversion of starting material. However, a reaction time of much over 5 hours begins to increase the amount of high boiling byproducts produced without significantly increasing the conversion or selectivity to neopentyldiamine. Therefore, the reaction conditions are preferably maintained for about 3 to 5 hours.

The partial pressure of hydrogen in the reactor during amination reaction is preferably between about 300 and 700 psig. Hydrogen partial pressure below about 300 psig decrease the rate of hydrogenation of the reaction intermediate and promotes formation of byproducts. Partial pressures of hydrogen higher than about 700 psig promotes hydrogenolysis and formation of low boiling byproducts. The more preferred hydrogen partial pressure is about 500 psig.

The following examples are set forth to illustrate the present invention and are not intended to limit the reasonable scope thereof.

EXAMPLE 1

This example illustrates the process of the present invention using a preferred catalyst. A 300-mL stainless steel autoclave was charged with 25 grams of neopentanolamine, 100 mL of anhydrous ammonia (77 grams, approximately 18 moles), and 5 grams of commercial nickel catalyst tablets. The catalyst is designated E-237 TR and is available from Calsicat Division of Mallinkrodt, Inc. This catalyst contains 55 weight percent nickel on an alumina support. The autoclave was charged with 500 psig of hydrogen and was brought up to 200° C. over approximately 42 minutes and was held at that temperature for 4 hours at 3,200 psig.

After this time, the autoclave was cooled and was slowly vented to relieve pressure. The contents of the autoclave were filtered and were analyzed by gas chromatography. The analysis showed that the product contained 3.7 percent isobutylamine, 84.3 percent neopentyldiamine, 5.1 percent unreacted neopentanolamine, and 6.9 percent higher boiling materials.

EXAMPLE 2

This example was performed as described in Example 1 with the exception that neopentylglycol was used in place of neopentanolamine. Analysis of the product showed it to contain 15.2 percent isobutylamine, 8.1 percent neopentyldiamine, 56.9 percent neopentylglycol, and 19.8 percent higher boiling materials. The results show that the process of the present invention using neopentanolamine is better.

EXAMPLE 3

This example was performed as described in Example 1 except that 5 grams of Ni-3266 from Harshaw Catalyst Company was used as catalyst. This catalyst contains 60 weight percent nickel on a Kieselguhr support. Analysis by gas chromatography showed that the product contained 3.3 percent isobutylamine, 1.1 percent neopentyldiamine, 88.0 percent unreacted neopentanolamine, and 7.6 percent higher boiling materials.

EXAMPLE 4

This example was performed as described in Example 2 using neopentylglycol as feed except that 5 grams of Ni-3266 nickel catalyst from Hawshaw Catalyst Company was used (catalyst of Example 3). Analysis of the crude product by gas chromatography showed 4.2 percent isobutylamine, 1.2 percent neopentyldiamine, 62.6 percent unreacted neopentyl lycol, and the remainder as higher boiling materials. This example further illustrates the importance in using neopentanolamine as feed. In this example, more feed is consumed without an improvement in the amount of product produced thus giving lower selectivity when compared to Example 3.

EXAMPLE 5

This example was performed using the conditions described in Example 1 except that 5 grams of Raney Ni-3100 was used as catalyst. This catalyst is an unsupported nickel catalyst. Analysis showed the product to contain 21.4 percent isobutylamine, 1.3 percent neopentyldiamine, 5.2 percent unreacted neopentanolamine, and 32.1 percent higher boiling materials.

EXAMPLE 6

This run was performed using 15 grams neopentylglycol, 100 mL anhydrous ammonia, and 5 grams of Raney Ni-3100 catalyst (catalyst of Example 5). Less neopentylglycol was used to keep the molar ratio of ammonia to hydroxyl groups the same as in the examples that use neopentanolamine. All other conditions were kept the same. Analysis showed that the crude product contained 23.2 percent isobutylamine, 15.5 percent neopentyldiamine, 12.9 percent neopentanolamine, 20.5 percent unreacted neopentyl glycol, and the remainder as higher boiling materials. The results confirm that the process of the present invention using neopentanolamine is a better more selective process.

EXAMPLE 7

This example was performed as described in Example 1 except that 5 grams of Co-0164 T supported cobalt catalyst from Harshaw Catalyst Company was used. This catalyst contains 25 weight percent cobalt on alumina support. Analysis of the crude product by gas chromatography showed 0.2 percent isobutylamine, 0.3 percent neopentyldiamine and the remainder as unreacted neopentanolamine.

The invention has been described in detail with particular reference to preferred embodiments thereof, however, it will be understood that variations and modifications can be made without departing from the reasonable scope thereof.

We claim:

1. A method for producing neopentyldiamine comprising contacting a high concentration of neopentanolamine with ammonia and hydrogen in the presence of a supported nickel catalyst under amination reaction conditions of a temperature of about 150° C. up to about 250° C. and a paressure of about 1,500 up to about 4,500 psig for a period of time of about 0.5 to about 5 hours.

2. The method according to claim 1 wherein the neopentanolamine is substantially free of neopentylglycol.

3. The method according to claim 1 wherein the neopentanolamine is between about 90 and about 100 weight % pure neopentanolamine.

4. The method according to claim 1 wherein the support for the said nickel containing catalyst is alumina.

5. The method according to claim 4 wherein the amount of nickel on said support is within the range of about 10 up to about 75 weight percent of the catalyst.

6. The method according to claim 5 wherein the catalyst contains about 55 weight percent nickel.

7. The method according to claim 1 wherein the molar ratio of ammonia to neopentanolamine is about 1 up to about 50 moles of ammonia per mole of neopentanolamine.

8. The method according to claim 1 wherein the weight ratio of neopentanolamine to catalyst is about 1:1 to about 1,000:1.

9. The method according to claim 1 wherein the mol ratio of ammonia to hydrogen is at least 1:1.

10. The method according to claim 1 wherein the reaction temperature is about 180° C. up to about 220° C., the reaction pressure is about 2,800 up to about 3,400 psig and said contacting under amination reaction conditions is maintained for about 3 up to about 5 hours.

11. A method for producing neopentyldiamine comprising contacting a high concentration of neopentanolamine with ammonia and hydrogen in the presence of a catalyst, which catalyst consists essentially of supported nickel; under amination reaction conditions of a temperature of about 150° C. up to about 250° C. and at a pressure of about 1,500 up to about 4,500 psig for about 0.5 to about 5 hours.

* * * * *